United States Patent [19]

Ogata et al.

[11] 4,330,472
[45] May 18, 1982

[54] META-SULFONAMIDO-BENZAMIDE DERIVATIVES

[75] Inventors: Masaru Ogata, Kobe; Hiroshi Matsumoto, Takatsuki, both of Japan

[73] Assignee: Shionogi & Co., Ltd., Osaka, Japan

[21] Appl. No.: 162,793

[22] Filed: Jun. 25, 1980

Related U.S. Application Data

[62] Division of Ser. No. 967,011, Dec. 6, 1978, which is a division of Ser. No. 872,584, Jan. 26, 1978, abandoned.

[30] Foreign Application Priority Data

Jan. 27, 1977 [JP] Japan .................................. 52-8443
Aug. 8, 1977 [JP] Japan .................................. 52-94884

[51] Int. Cl.³ .................................................. C07D 207/08
[52] U.S. Cl. ...................................... 548/567; 424/274
[58] Field of Search ............. 546/185; 260/326.8, 260/326.47

[56] References Cited

U.S. PATENT DOCUMENTS

4,021,567  5/1977  Kaplan ..................... 546/185

*Primary Examiner*—Anton H. Sutto
*Assistant Examiner*—D. B. Springer
*Attorney, Agent, or Firm*—Wenderoth, Lind & Ponack

[57] ABSTRACT

Meta-sulfonamido-benzamide derivatives of the formula:

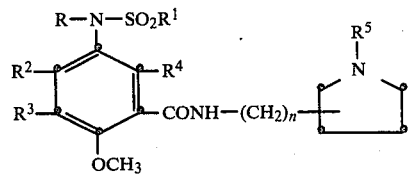

[wherein
R is a hydrogen atom or a lower alkyl, cyano, or lower alkanesulfonyl group;
$R^1$ is a lower alkyl, phenyl, amino, lower alkylamino, di(lower)alkylamino, or $C_4$–$C_5$ alkyleneamino group;
$R^2$ is a hydrogen or halogen atom or a lower alkyl, di(lower)alkylamino, or lower alkoxy group;
$R^3$ is a hydrogen atom or a methyl or methoxy group;
$R^4$ is a hydrogen or halogen atom;
$R^5$ is a lower alkyl, lower alkenyl, $C_3$–$C_6$ cycloalkyl, benzyl, or halogenobenzyl group; and n is 1 or zero]

or their acid addition salts, showing pharmacological activity such as anti-emetic or psychotropic activity, are provided via several routes.

2 Claims, No Drawings

META-SULFONAMIDO-BENZAMIDE DERIVATIVES

This is a division of application Ser. No. 967,011, filed Dec. 6, 1978, which is a division of application Ser. No. 872,584, filed Jan. 26, 1978, now abandoned.

The present invention relates to meta-sulfonamido-benzamide derivatives and a process for the production thereof.

The meta-sulfonamido-benzamide derivatives provided by the present invention are compounds of the formula:

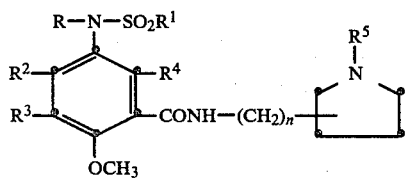   I

[wherein
R is a hydrogen atom or a lower alkyl, cyano, or lower alkanesulfonyl group;
$R^1$ is a lower alkyl, phenyl, amino, lower alkylamino, di(lower)alkylamino, or $C_4$–$C_5$ alkyleneamino group;
$R^2$ is a hydrogen or halogen atom or a lower alkyl, di(lower)alkylamino, or lower alkoxy group;
$R^3$ is a hydrogen atom or a methyl or methoxy group;
$R^4$ is a hydrogen or halogen atom;
$R^5$ is a lower alkyl, lower alkenyl, $C_3$–$C_6$ cycloalkyl, benzyl, or halogenobenzyl group; and
n is 1 or zero]
and their acid addition salts.

As used in this specification, the term "lower alkyl" means a straight chain or branched-chain alkyl group which preferably contains from 1 to 6 carbon atoms (e.g. methyl, ethyl, propyl, isopropyl, butyl, t-butyl, pentyl, hexyl and the like). The methyl group is preferred, except that the ethyl group is the preferred lower alkyl group for $R^5$. The term "lower alkoxy group" means a straight or branched alkoxy group which preferably contains from 1 to 6 carbon atoms (e.g. methoxy, ethoxy, propoxy, isopropoxy, butoxy, pentoxy group). The methoxy group is the preferred lower alkoxy group. The term "lower alkanesulfonyl" means a straight or branched alkanesulfonyl group preferably containing from 1 to 6 carbon atoms (e.g. methanesulfonyl, ethanesulfonyl, propanesulfonyl, butanesulfonyl, pentanesulfonyl, and the like). The methanesulfonyl group is the preferred lower alkanesulfonyl group. The term "lower-alkylamino" means a straight or branched alkylamino group of 1 to 6 carbon atoms (e.g. methylamino, ethylamino, propylamino, isopropylamino, butylamino, pentylamino, and the like), and the methylamino group is preferred. The term "di(lower)alkylamino" means a $C_2$–$C_{12}$ dialkylamino group in which the two alkyl groups are the same or different (e.g. dimethylamino, diethylamino, methylethylamino, ethylpropylamino, methylbutylamino, dibutylamino, dihexylamino, and the like). The dimethylamino group is preferred. The term "lower alkenyl" means a straight or branched alkenyl group preferably containing from 2 to 6 carbon atoms (e.g. vinyl, allyl, butenyl, pentenyl, and the like). The term "halogen" means fluorine, chlorine, bromine or iodine. The preferred halogen for $R^2$ is chlorine or fluorine. The term "$C_3$–$C_6$ cycloalkyl" means cyclopropyl, cyclobutyl, cyclopentyl, or cyclohexyl. The cyclohexyl group is the preferred cycloalkyl group. The term "$C_4$–$C_5$ alkyleneamino group" means a pyrrolidino or piperidino group, and the piperidino group is preferred. The term "halogenobenzyl" denoted by $R^5$ includes an o-halogenobenzyl group such as o-chlorobenzyl or o-fluorobenzyl and a p-halogenobenzyl group such as p-chlorobenzyl or p-fluorobenzyl.

Preferred compounds of formula I hereinbefore are those of the formula:

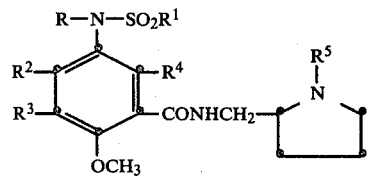   Ia

[wherein
R is a hydrogen atom or a lower alkyl, cyano, or lower alkanesulfonyl group;
$R^1$ is a lower alkyl, phenyl, amino, lower alkylamino, or di(lower)alkylamino group;
$R^2$ is a hydrogen or halogen atom or a lower alkyl, di(lower)alkylamino, or lower alkoxy group;
$R^3$ is a hydrogen atom or a methyl or methoxy group;
$R^4$ is a hydrogen or halogen atom; and
$R^5$ is a lower alkyl, lower alkenyl, $C_3$–$C_6$ cycloalkyl, benzyl, or halogenobenzyl group]
or their acid addition salts.

More preferred compounds of formula Ia hereinbefore are those in which R, $R^3$, and $R^4$ each is a hydrogen atom; $R^1$ is a lower alkyl, phenyl, amino, methylamino or dimethylamino group; $R^2$ is a hydrogen or chlorine atom or a methyl group; and $R^5$ is an ethyl or halogenobenzyl group.

Examples of compounds of formula I hereinbefore are:
N-(1-ethyl-2-pyrrolidinylmethyl)-2-methoxy-4-chloro-5-methanesulfonamidobenzamide,
N-(1-ethyl-2-pyrrolidinylmethyl)-2-methoxy-5-methanesulfonamidobenzamide,
N-(1-ethyl-2-pyrrolidinylmethyl)-2-methoxy-5-benzenesulfonamidobenzamide,
N-(1-ethyl-2-pyrrolidinylmethyl)-2-methoxy-5-(N-cyanomethanesulfonamido)benzamide,
N-(1-ethyl-2-pyrrolidinylmethyl)-2-methoxy-5-(N-methylethanesulfonamido)benzamide,
N-(1-ethyl-2-pyrrolidinylmethyl)-2-methoxy-4-fluoro-5-methanesulfonamidobenzamide,
N-(1-ethyl-2-pyrrolidinylmethyl)-2-methoxy-4-chloro-5-ethanesulfonamidobenzamide,
N-(1-ethyl-2-pyrrolidinylmethyl)-2-methoxy-4-chloro-5-propanesulfonamidobenzamide,
N-(1-ethyl-2-pyrrolidinylmethyl)-2-methoxy-4-dimethylamino-5-methanesulfonamidobenzamide,
N-(1-ethyl-2-pyrrolidinylmethyl)-2-methoxy-5-ethanesulfonamidobenzamide,
N-(1-ethyl-2-pyrrolidinylmethyl)-2-methoxy-5-dimethylaminosulfonamidobenzamide,
N-(1-ethyl-2-pyrrolidinylmethyl)-2-methoxy-5-butanesulfonamidobenzamide,
N-(1-ethyl-2-pyrrolidinylmethyl)-2,3-dimethoxy-5-methanesulfonamidobenzamide, N-(1-ethyl-2-pyrrolidinylmethyl)-2,4-dimethoxy-5-methanesulfonamidobenzamide,
N-(1-ethyl-2-pyrrolidinylmethyl)-2-methoxy-4-methyl-5-ethanesulfonamidobenzamide,
N-(1-ethyl-2-pyrrolidinylmethyl)-2-methoxy-4-methyl-5-methanesulfonamidobenzamide,
N-(1-ethyl-2-pyrrolidinylmethyl)-2-methoxy-4-ethyl-5-methanesulfonamidobenzamide,
N-(1-ethyl-2-pyrrolidinylmethyl)-2-methoxy-3-methyl-5-ethanesulfonamidobenzamide,
N-(1-ethyl-2-pyrrolidinylmethyl)-2-methoxy-4-ethyl-5-ethanesulfonamidobenzamide,
N-(1-ethyl-2-pyrrolidinylmethyl)-2-methoxy-3-methyl-5-methanesulfonamidobenzamide,
N-(1-ethyl-2-pyrrolidinylmethyl)-2-methoxy-4-methyl-5-dimethylaminosulfonamidobenzamide,
N-(1-ethyl-2-pyrrolidinylmethyl)-2-methoxy-6-chloro-5-methanesulfonamidobenzamide,
N-(1-cyclohexyl-3-pyrrolidinylmethyl)-2-methoxy-5-methanesulfonamidobenzamide,
N-(1-ethyl-2-pyrrolidinylmethyl)-2-methoxy-4-chloro-5-(N-methylmethanesulfonamido)benzamide,
N-(1-ethyl-2-pyrrolidinylmethyl)-2-methoxy-4-methyl-5-t-butylaminosulfonamidobenzamide,
N-(1-ethyl-2-pyrrolidinylmethyl)-2-methoxy-4-methyl-5-aminosulfonamidobenzamide,
N-(1-ethyl-2-pyrrolidinylmethyl)-2-methoxy-4-chloro-5-t-butylaminosulfonamidobenzamide,
N-(1-ethyl-2-pyrrolidinylmethyl)-2-methoxy-4-chloro-5-aminosulfonamidobenzamide,
N-(1-ethyl-2-pyrrolidinylmethyl)-2-methoxy-4-chloro-5-piperidinosulfonamidobenzamide,
N-(1-ethyl-2-pyrrolidinylmethyl)-2-methoxy-4-methyl-5-methylaminosulfonamidobenzamide,
N-(1-ethyl-2-pyrrolidinylmethyl)-2-methoxy-5-t-butylaminosulfonamidobenzamide,
N-(1-ethyl-2-pyrrolidinylmethyl)-2-methoxy-5-aminosulfonamidobenzamide,
N-(1-allyl-2-pyrrolidinylmethyl)-2-methoxy-4-methyl-5-methanesulfonamidobenzamide,
N-(1-benzyl-2-pyrrolidinylmethyl)-2-methoxy-4-methyl-5-methanesulfonamidobenzamide,
N-(1-allyl-2-pyrrolidinylmethyl)-2-methoxy-4-chloro-5-methanesulfonamidobenzamide, and
N-(1-p-fluorobenzyl-2-pyrrolidinylmethyl)-2-methoxy-4-chloro-5-methanesulfonamidobenzamide.

According to the process provided by the present invention, the meta-sulfonamido-benzamide derivatives (i.e. the compounds of formula I hereinbefore and their acid addition salts) are manufactured by a. reacting a dihalogeno compound of the formula:

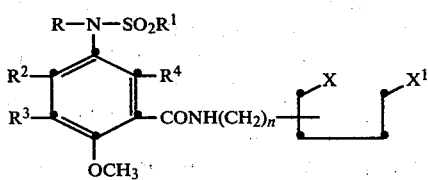

[wherein X and $X^1$ each is a halogen atom; and R, $R^1$, $R^2$, $R^3$, $R^4$, and n each has the significance given earlier] with an amine of the formula:

$$R^5—NH_2 \qquad \qquad III$$

[wherein $R^5$ has the significance given earlier];

b. reacting an anilino compound of the formula:

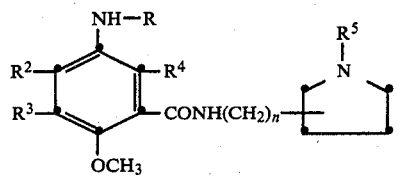

[wherein R, $R^2$, $R^3$, $R^4$, $R^5$, and n each has the significance given earlier] with a sulfonating agent of the formula:

$$A—SO_2R^1 \qquad \qquad V$$

[wherein A is a reactive residue and $R^1$ has the significance given earlier]; or c. reacting a benzoic derivative of the formula:

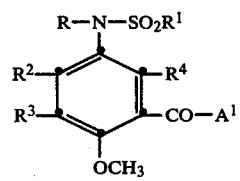

[wherein $A^1$ is a reactive residue, and R, $R^1$, $R^2$, $R^3$, and $R^4$ each has the significance given earlier] with a diamino compound of the formula:

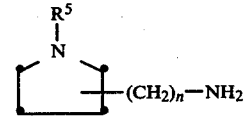

[wherein $R^5$ and n each has the significance given earlier] and, if desired, converting a free base obtained into an acid addition salt or converting an acid addition salt obtained into a free base or into a different acid addition salt.

The reaction of a dihalogeno compound of formula II with an amine of formula III can be carried out in the presence or absence of a suitable solvent (e.g. water, ethanol, methylene chloride, pyridine, or triethylamine) at a temperature above room temperature (e.g. 15° C. to 100° C.). The amine of formula III illustratively includes methylamine, ethylamine, propylamine, butylamine, allylamine, butenylamine, cyclopropylamine, cyclohexylamine, benzylamine, o-chlorobenzylamine, and p-fluorobenzylamine.

The reaction of an anilino compound of formula IV with a sulfonating agent of formula V can be carried out in accordance with methods known per se. The sulfonating agent of formula V illustratively includes a halogenide (e.g. chloride, bromide, iodide), an active ester (e.g. p-nitrophenyl ester, benzyl ester, trityl ester), and an anhydride (e.g. methanesulfonic anhydride, or ethanesulfonic anhydride) of a prescribed sulfonic acid having the moiety of $R^1$. The sulfonation is carried out in an inert solvent (e.g. methylene chloride, benzene, tetrahydrofuran, or dioxane) in the presence of a base such as an organic base (e.g. triethylamine or pyridine) or an inorganic base (e.g. potassium carbonate or sodium hydrogencarbonate) at a temperature below or above room temperature (e.g. temperature in the range of 0° C. to 100° C.). Alternatively, the organic base may be used in the form of the solvent. The reaction can generally result in a high yield. When R is a lower alkyl, cyano, or lower alkanesulfonyl group, only 1 mol equivalent of the group —SO$_2$R$^1$ can be introduced under the sulfonation of this invention. Still, when R is a hydrogen atom, 2 mol equivalents of the group —SO$_2$R$^1$ may be optionally introduced but the second group can be easily replaced by a hydrogen atom only by treating the resultant product with an inorganic base such as aqueous alkali hydroxide (e.g. aqueous sodium hydroxide or potassium hydroxide).

A compound of formula I hereinbefore in which R is a hydrogen atom may be subjected to alkylation according to methods known per se. Still, a compound of formula I in which R is a lower alkanesulfonyl group and R$^1$ is a di(lower)alkylamino group, if desired, may be treated with an inorganic base such as aqueous alkali hydroxide (e.g. aqueous sodium hydroxide) for removing the lower alkanesulfonyl group being liable to hydrolysis. Additionally, the product of formula I hereinbefore in which R$^1$ is a t-butylamino group may be treated with trifluoroacetic acid for removal of the tertiary butyl group whereby the compound of formula I hereinbefore in which R$^1$ is an amino group is obtained.

The reaction of a benzoic derivative of formula VI with a diamino compound of formula VII can be carried out in accordance with methods which are known per se in peptide chemistry; for example, by the mixed anhydride, azide, ester, or acid chloride method. For example, a benzoic derivative of formula VI in which the reactive residue is in the form of an ester group (e.g. the lower alkyl, p-nitrophenyl, or 2,4-dinitrophenyl ester group) can be condensed with an appropriate compound of formula VII at ordinary temperature (e.g. 15° C. to 25° C.). In another method, an appropriate benzoic derivative of formula VI in which the reactive residue is in the form of an acid chloride can be condensed with a diamino compound of formula VII in the presence of a base such as an organic base (e.g. triethylamine or pyridine) or an inorganic base (e.g. sodium carbonate, potassium hydrogencarbonate, or sodium hydroxide) at ordinary temperature.

The starting materials of formula II hereinbefore can be prepared, for example, by reacting a tetrahydrofuryl compound of the formula:

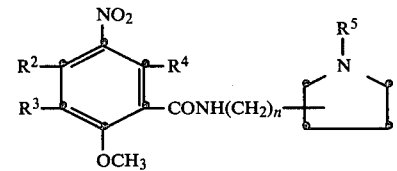

VIII

[wherein R, R$^1$, R$^2$, R$^3$, R$^4$, and n each has the significance given earlier] with a halogenating agent (e.g. thionyl chloride) according to methods known per se. The halogenation may be carried out in an inert solvent (e.g. chloroform, benzene, acetonitrile, methylene chloride, or carbon tetrachloride) at a temperature above room temperature (e.g. ca. 25° C. to ca. 200° C.).

The tetrahydrofuryl compound of formula VIII can be prepared by reacting a compound of the formula:

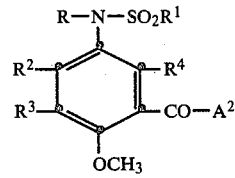

IX

[wherein A$^2$ is a reactive residue; and R, R$^1$, R$^2$, R$^3$, and R$^4$ each has the significance given earlier] with a tetrahydrofuran derivative of the formula:

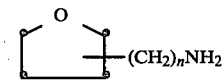

X

[wherein n has the significance given earlier] in accordance with methods known per se. The condensation can be carried out in an inert solvent (e.g. benzene, toluene, methylene chloride, dimethylformamide, or tetrahydrofuran) at a temperature below or above room temperature (e.g. 0° C. to ca. 100° C.).

The compound of formula IX can be prepared by subjecting a compound of the formula:

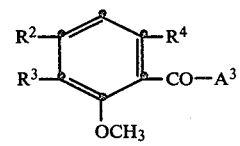

XI

[wherein A$^3$ is a hydroxy group or a reactive residue; R$^2$, R$^3$, and R$^4$ each has the significance given earlier] to nitration, reduction of the nitro group into an amino group, introduction of the group R, and sulfonation given earlier in an appropriate combination.

The starting materials of formula IV hereinbefore can be prepared, for example, by reducing a nitro compound of the formula:

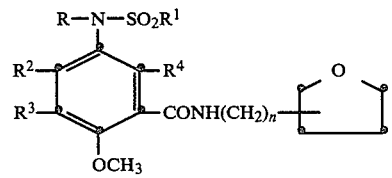

XII

[wherein R$^2$, R$^3$, R$^4$, R$^5$, and n each has the significance given earlier] by methods known per se for converting a nitro group into an amino group; e.g. catalytic hydrogenation over palladium/carbon, platinum oxide, or Raney nickel; tin/hydrochloric acid or iron/hydrochloric acid reduction. If necessary, a resulting anilino compound is subjected to introduction of the group R by methods known per se. Thus, the lower alkyl group denoted by R can be introduced by monoalkylation of an aromatic primary amine, adopting a lower alkyl iodide or di(lower)alkyl sulfate method or a combination of N-acylation and reduction of a carbonyl group.

The lower alkanesulfonyl group denoted by R can be introduced according to the method given earlier for introduction of the group —SO$_2$R$^1$. The cyano group denoted by R can be introduced, for example, by reacting a corresponding anilino compound with ethyl orthoformate and sodium azide in acetic acid and treating the resulting tetrazolyl compound with a base (e.g. aqueous sodium hydroxide) at a temperature above room temperature (e.g. ca. 15° C. to ca. 120° C.).

The nitro compound of formula XII can be obtained by nitrating a compound of formula XI by methods known per se and condensing a resulting compound of the formula:

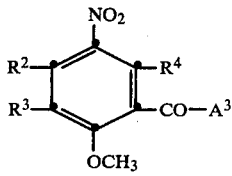
XIII

[wherein $R^2$, $R^3$, $R^4$, and $A^3$ each has the significance given earlier] with a diamine of formula VII according to the method given earlier for the condensation of a benzoic derivative of formula VI with a diamine of formula VII.

The starting materials of formula VI hereinbefore can be prepared, for example, by reacting a compound of the formula:

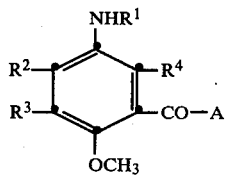
XIV

[wherein $R^1$, $R^2$, $R^3$, $R^4$, and A each has the significance given earlier] with a sulfonating agent of formula V according to the method given earlier for the condensation of an anilino compound of formula IV with a sulfonating agent of formula V. The compound of formula XIV can be prepared by reducing a compound of formula XIII to a corresponding anilino compound and, if desired, introducing the group R into the amino group of the anilino compound according to the method given earlier.

The compounds of formula I hereinbefore form acid addition salts with inorganic acids (e.g. hydrochloric acid, hydrobromic acid, sulfuric acid, phosphoric acid nitric acid, thiocyanic acid; and the like) and with organic acids (e.g. acetic acid, oxalic acid, succinic acid, maleic acid, malic acid, phthalic acid, tartaric acid, citric acid, methanesulfonic acid, toluenesulfonic acid, and the like). The acid addition salts can be prepared in accordance with well known methods; for example, by treating a base of formula I with an appropriate acid. An acid addition salt may be converted into a different acid addition salt by methods known per se. Of these acid addition salts, the pharmaceutically acceptable acid addition salts are preferable.

The compounds of formula I hereinbefore and their acid addition salts have anti-emetic and psychotropic activity. Thus, they are useful as anti-peptic-ulcer agents and neuroleptics.

The anti-emetic activity of the meta-sulfonamidobenzamide derivatives in this invention are shown by administering them orally to male beagle dogs of 10 to 20 months age, treating subcutaneously with 0.1 mg/kg of apomorphine, and examining the number vomiting in 30 minutes. The result is shown by an $ED_{50}$ (mg/kg) which means a dose to induce 50% inhibition of vomiting. [Janssen, P. A. J. et al., Arzneim.-Forsch. 18 (3) 261–279 (1968)]

The psychotropic activity can be shown in the antagonism in DS male mice to apomorphine-induced hyperactivity on spontaneous mobilities. This test is carried out by administering orally a test compound to the mice, examining an hour later an amount of spontaneous mobilities for 15 minutes, administering subcutaneously 2.5 mg/kg of metamphetamine to them and examining another amount of spontaneous mobilities for 10 minutes. The result is shown by an $ED_{50}$ (mg/kg) which means a dose to induce 50% inhibition on spontaneous mobilities. [Janssen, P. A. J. et al., ibid.]

The compounds of formula I and their pharmaceutically acceptable acid addition salts may be used as medicaments; for example, in the form of pharmaceutical preparations which contain them in combination with a compatible pharmaceutical carrier material. This carrier material can be an organic or inorganic carrier material suitable for enteral or parenteral administration (e.g. water, lactose, gelatin, starches, magnesium stearate, talc, vegetable oils, gums, polyalkyleneglycols, petroleum jelly, etc.). The pharmaceutical preparations can be made up in a solid form (e.g. tablets, dragees, capsules, etc.) or in a liquid form (e.g. solutions, suspensions, or emulsions). Pharmaceutical preparations in a form adopted for injection purposes may be subjected to conventional pharmaceutical operations such as sterilization and/or may contain conventional pharmaceutical adjuvants such as preservatives, stabilizers, wetting agents, emulsifiers, buffers, etc.

The dosage in which the compounds of formula I and their pharmaceutically acceptable acid addition salts may be administered can vary depending upon the requirements of the patient and the directions of the attending physician. A preferred daily dosage for human adults is of the order of about 30 mg to about 350 mg for oral administration.

Benzamide derivatives including N-(1-ethyl-2-pyrrolidinylmethyl)-2-methoxy-5-sulfamoylbenzamide (sulpiride) have been known as an anti-peptic-ulcer agent or anti-depressant.

Presently preferred and practical embodiments of the present invention are illustratively shown in the following examples.

EXAMPLE 1

(1) A mixture of 2,4-dichlorobenzoic acid (67.4 g), absolute methanol (135 ml), and copper powder (3.37 g) is refluxed for 6–7 hours while introducing gaseous dimethylamine. The reaction mixture is mixed with a large amount of water, acidified with hydrochloric acid, and shaken with ether. The organic layer is washed with water, dried over sodium sulfate, and evaporated to remove the solvent. The residue is washed with isopropyl ether and filtered to give 2-methoxy-4-chlorobenzoic acid (43.6 g) as crystals melting at 139.5° to 141° C.

(2) Above product (3.25 g) is added dropwise to fuming nitric acid (specific gravity; 1.52) (10 ml) at −30° C. with stirring, and the resultant mixture is stirred for 10 minutes. The reaction mixture is poured into icy water and shaken with chloroform/methanol. The organic layer is washed with water, dried over sodium sulfate, and evaporated to remove the solvent. The residue is washed with isopropyl ether and filtered to give 2-methoxy-4-chloro-5-nitrobenzoic acid (2.85 g) as crystals melting at 184° to 185° C. (Helv. Chim. Acta., 40, 369 (1957)).

NMR: $\delta_{ppm}^{d_6\text{-}DMSO}$ 4.00 s. 3H, OC$\underline{H}_3$; 7.48 s. 1H, H$_3$; 8.40 s. 1H, H$_6$; 12.3–15 br. 1H, COO$\underline{H}$.

(3) A mixture of 2-methoxy-4-chloro-5-nitrobenzoic acid (900 mg) and thionyl chloride (5 ml) is refluxed for 30 minutes, and the resultant mixture is evaporated to remove the thionyl chloride. The residue is mixed with benzene and evaporated to remove the benzene. The residue is mixed with triethylamine (790 mg) and dry methylene chloride (9 ml), and a solution of 1-ethyl-2-aminomethylpyrrolidine (750 mg) and methylene chloride (4 ml) is added dropwise thereto with ice cooling and stirring. The resultant mixture is stirred at room temperature for 15 minutes. The reaction mixture is mixed with aqueous sodium hydrogencarbonate and shaken with methylene chloride. The organic layer is washed with water, dried over sodium sulfate, and evaporated to remove the solvent. The residue is mixed with ether and shaken with dilute hydrochloric acid. The aqueous layer is made alkaline with aqueous sodium hydrogencarbonate, and shaken with methylene chloride. The organic layer is washed with water, dried over sodium sulfate, and evaporated to remove the solvent. The residue is recrystallized from ethyl acetate/isopropyl ether to give N-(1-ethyl-2-pyrrolidinylmethyl)-2-methoxy-4-chloro-5-nitrobenzamide (679 mg) as crystals melting at 107° to 108° C.

Anal. Cald. for $C_{15}H_{20}O_4N_3Cl$: C,52.71; H,5.90; N,12.29; Cl,10.37. Found: C,52.90; H,6.00; N,12.28; Cl,10.63.

(4) Above product (7.33 g) is mixed with a solution of conc. hydrochloric acid (36.7 ml) and water (73.3 ml), and the resultant mixture is heated at 50° C., mixed with tin chips (7.7 g), and stirred at 50° C. for 4 hours. After cooling, the reaction mixture is made alkaline with aqueous sodium hydroxide and shaken with methylene chloride. The organic layer is washed with water, dried over sodium sulfate, and evaporated to remove the solvent. The residue is chromatographed on a column of alumina, which is eluted with methylene chloride. The eluate is evaporated to remove the solvent. The residue is washed with isopropyl ether/petroleum ether to give N-(1-ethyl-2-pyrrolidinylmethyl)-2-methoxy-4-chloro-5-aminobenzamide (5.38 g). The product is recrystallized from isopropyl ether/petroleum ether to give the crystals melting at 85° to 86.5° C.

Anal. Calcd. for $C_{15}H_{22}O_2N_3Cl$: C,57.78; H,7.11; N,13.48; Cl,11.37. Found: C,57.63; H,7.18; N,13.55; Cl,11.66.

(5) To a solution of above product (4.1 g) and triethylamine (2.93 g) in dry methylene chloride (41 ml), a solution of methanesulfonyl chloride (3.18 g) and dry methylene chloride (8.2 ml) is added dropwise with ice cooling. After removing the ice bath, the reaction mixture is stirred at room temperature for 45 minutes. The reaction mixture is made alkaline with aqueous sodium hydrogencarbonate and shaken with methylene chloride. The organic layer is washed with water, dried over sodium sulfate, and evaporated to remove the solvent. The residue is washed with ethyl acetate/isopropyl ether to give N-(1-ethyl-2-pyrrolidinylmethyl)-2-methoxy-4-chloro-5-N,N-bis(methanesulfonyl)aminobenzamide (5.83 g) as crystals melting at 153° to 155° C.

Anal. Calcd. for $C_{17}H_{26}O_6N_3S_2Cl$: C,43.63; H,5.60; N,8.98; S,13.70; Cl,7.58. Found: C,43.37; H,5.73; N,8.98; S,13.79; Cl,7.72.

(6) A suspension of above product (5.75 g) in 10% sodium hydroxide (57.5 ml) is stirred with heating at 50° C. for 30 minutes. After the cooling, the reaction mixture is acidified with conc. hydrochloric acid, made alkaline with aqueous sodium hydrogencarbonate, saturated with sodium chloride, and shaken with methylene chloride. The organic layer is washed with saturated brine, dried over sodium sulfate, and evaporated to remove the methylene chloride. The residue is chromatographed on a column of alumina, which is eluted with methylene chloride singly and with 2% methanol/methylene chloride and evaporated to remove the solvent. The residue is washed with ethyl acetate/isopropyl ether to give N-(1-ethyl-2-pyrrolidinylmethyl)-2-methoxy-4-chloro-5-methanesulfonamidobenzamide (4.3 g), which is recrystallized from ethyl acetate/isopropyl ether to give colorless prism crystals melting at 126° to 127.5° C.

Anal. Calcd. for $C_{16}H_{24}O_4N_3SCl$: C,49.29; H,6.20; N,10.78; S,8.22; Cl,9.09. Found: C,49.17; H,6.22; N,10.77; S,8.28; Cl,9.26.

EXAMPLE 2

(1) To a mixture of N-(1-ethyl-2-pyrrolidinylmethyl)-2-methoxy-5-aminobenzamide (700 mg), triethylamine (1.02 g), and methylene chloride (14 ml), methanesulfonyl chloride (870 mg) is added dropwise with stirring at room temperature, and the resultant mixture is stirred at room temperature for 1 hour. The reaction mixture is mixed with water, made alkaline with aqueous sodium hydrogencarbonate, and shaken with methylene chloride. The organic layer is washed with water, dried over sodium sulfate, and evaporated to remove the methylene chloride. The residue is chromatographed on a column of alumina, which is eluted with methylene chloride. After evaporating the solvent from eluate, the residue is recrystallized from ethyl acetate/isopropyl ether to give N-(1-ethyl-2-pyrrolidinylmethyl)-2-methoxy-5-N,N-bis(methanesulfonyl)aminobenzamide (582 mg). The product is recrystallized from ethyl acetate to give crystals melting at 160° to 161° C.

Anal. Calcd. for $C_{17}H_{27}O_6N_3S_2$: C,47.0; H,6.28; N,9.69; S,14.79. Found: C,47.25; H,6.30; N,9.55; S,14.99.

Then, as an eluent is used 3% methanol/methylene chloride, whereby N-(1-ethyl-2-pyrrolidinylmethyl)-2-methoxy-5-methanesulfonamidobenzamide is obtained. The eluate is evaporated, and the residue is crystallized from ethyl acetate/isopropyl ether to give the product (148 mg), which is recrystallized from ethyl acetate to give crystals melting at 170° to 171.5° C.

Anal. Calcd. for $C_{16}H_{25}O_4N_3S$: C,54.06; H,7.09; N,11.82; S,9.02. Found C,54.35; H,7.18; N,11.74; S,9.29.

(2) A suspension of N-(1-ethyl-2-pyrrolidinylmethyl)-2-methoxy-5-N,N-bis(methanesulfonyl)aminobenzamide (290 mg) in 10% sodium hydroxide (2.9 ml) and methanol (2.9 ml) is warmed for 5 minutes on a water bath, whereby a clear solution is obtained. After evaporating the solvent, the residue is mixed with icy water, acidified with 6 N hydrochloric acid, made weakly alkaline with aqueous sodium hydrogencarbonate, and shaken with methylene chloride. The organic layer is washed with water, dried over sodium sulfate, and evaporated to remove the solvent. The residue is washed with ethyl acetate/isopropyl ether to give N-(1-ethyl-2-pyrrolidinylmethyl)-2-methoxy-5-methanesulfonamidobenzamide (148 mg), which is recrystallized from ethyl acetate/isopropyl ether to give crystals melting at 170° to 171.5° C.

EXAMPLE 3

(1) To a mixture of N-(1-ethyl-2-pyrrolidinylmethyl)-2-methoxy-5-aminobenzamide (700 mg), methylene chloride (14 ml), and triethylamine (1.03 g), benzenesulfonyl chloride (1.35 g) is added at room temperature, and the resultant mixture is allowed to stand at room temperature. The reaction mixture is mixed with water, made alkaline with aqueous sodium hydrogencarbonate, and shaken with methylene chloride. The organic layer is washed with water, dried over sodium sulfate, and evaporated to remove the solvent. The residue is dissolved in methylene chloride, and chromatographed on a column of alumina, which is eluted with methylene chloride. After evaporating the methylene chloride from the eluate, the residue is recrystallized from ethyl acetate/isopropyl ether to give N-(1-ethyl-2-pyrrolidinylmethyl)-2-methoxy-5-N,N-bis(benzenesulfonyl)aminobenzamide (839 mg) as crystals melting at 166° to 170° C.

Anal. Calcd. for $C_{27}H_{31}O_6N_3S_2 \cdot \frac{1}{2}H_2O$: C,57.23; H,5.69; N,7.42; S,11.32. Found: C,57.26; H,5.69; N,7.20; S,11.50.

(2) A mixture of above product (500 mg), 10% sodium hydroxide (7.5 ml), and methanol (7.5 ml) is warmed on a water bath for 5 minutes. After evaporating the methanol from the reaction mixture, the residue is mixed with water, acidified with hydrochloric acid, made alkaline again with aqueous sodium hydrogencarbonate, and shaken with methylene chloride. The organic layer is dried and evaporated to remove the solvent. The residue is washed with ethyl acetate/isopropyl ether to give N-(1-ethyl-2-pyrrolidinylmethyl)-2-methoxy-5-benzenesulfonamidobenzamide (325 mg). This product is recrystallized from ethyl acetate to give crystals melting at 177° to 178° C.

Anal. Calcd. for $C_{21}H_{27}O_4N_3S$: C,60.41; H,6.52; N,10.06; S,7.68. Found: C,60.40; H,6.52; N,9.95; S,7.74.

EXAMPLE 4

(1) A mixture of N-(1-ethyl-2-pyrrolidinylmethyl)-2-methoxy-5-nitrobenzamide (1.5 g), platinum oxide (150 mg), and methanol (30 ml) is subjected to catalytic hydrogenation by shaking under hydrogen stream. The reaction mixture is worked up in a conventional manner and evaporated to remove the methanol. The residue is mixed with sodium azide (500 mg), ethyl orthoformate (5 ml), and acetic acid (5 ml), and the resultant mixture is heated at 80° C. for 1 hour. The reaction mixture is mixed with icy water, made alkaline with sodium carbonate, and shaken with methylene chloride. The organic layer is washed with water, dried over sodium sulfate, and evaporated to remove the solvent. The residue is crystallized from ethyl acetate/isopropyl ether to give N-(1-ethyl-2-pyrrolidinylmethyl)-2-methoxy-5-(1H-tetrazol-1-yl)benzamide (1.3 g) as crystals melting at 171° to 174° C.

Anal. Calcd. for $C_6H_{22}O_2N_6$: C,58.16; H,6.71; N,25.44. Found: C,57.87; H,6.71; N,25.36.

(2) A mixture of above product (1.3 g), ethanol (9.8 ml), water (3.3 ml), and 10% sodium hydroxide (6.5 ml) is heated at 80° C. for 40 minutes. After evaporating the ethanol, the residue is acidified with 6 N hydrochloric acid, made alkaline with triethylamine, salted out with sodium chloride, and shaken with 5% methanol/methylene chloride. The organic layer is dried over sodium sulfate and evaporated to remove the solvent. The residue is washed with ethyl acetate to give N-(1-ethyl-2-pyrrolidinylmethyl)-2-methoxy-5-cyanoaminobenzamide (641 mg), which is recrystllized from ethyl acetate to give crystals melting at 134° to 139° C.

Anal. Cald. for $C_{16}H_{22}O_2N_4$:C,63.55; H,7.30; N,18.53. Found: C,63.53; H,7.41;N,18.37.

(3) A solution of above product (300 mg) and pyridine (1.5 ml) is mixed with methanesulfonyl chloride (340 mg) at room temperature, and the resultant mixture is stirred at room temperature for 2 hours, and stirred at 50° C. for 30 minutes. The reaction mixture is mixed with aqueous sodium carbonate and shaken with methylene chloride. The organic layer is washed with water, dried over sodium sulfate, and evaporated to remove the solvent. The residue is dissolved in methylene chloride and chromatographed on a column of alumina, which is eluted with methylene chloride. After evaporating the methylene chloride from the eluate, the residue is washed with ether/isopropyl ether and recrystallized to give N-(1-ethyl-2-pyrrolidinylmethyl)-2-methoxy-5-(N-cyanomethanesulfonamido)benzamide (99 mg) as crystals melting at 50° to 54° C.

Anal. Calcd. for $C_{17}H_{24}O_4N_4S$: C,53.67; H,6.36; N,14.73; S,8.43. Found: C,53.27; H,6.39; N,14.40; S,8.35.

EXAMPLE 5

To a solution of N-(1-ethyl-2-pyrrolidinylmethyl)-2-methoxy-5-ethanesulfonamidobenzamide (266 mg) in dry acetone (7 ml), potassium carbonate and dimethylsulfate (100 mg) are added, and the resultant mixture is refluxed for 30 minutes. After evaporating the acetone, the residue is mixed with water and shaken with methylene chloride. The organic layer is washed with water, dried over sodium sulfate, and evaporated to remove the solvent. The residue is dissolved in methylene chloride, and the resultant mixture is chromatographed on a column of alumina, which is eluted with methylene chloride. After evaporating the eluate to remove the methylene chloride, the residue is washed with isopropyl ether and recrystallized from ethyl acetate/isopropyl ether in that order to give N-(1-ethyl-2-pyrrolidinylmethyl)-2-methoxy-5-(N-methylethanesulfonamido)-benzamide (74 mg) as crystals melting at 85° to 87° C.

Anal. Calcd. for $C_{18}H_{29}O_4N_3S$: C,56.37; H,7.62; N,10.96; S,8.36. Found: C,56.55; H,7.68; N,10.80; S,8.61.

EXAMPLES 6–23

Using the following starting materials (IV), the reactions are effected as in Example 1, whereby the corresponding products (I) are obtained.

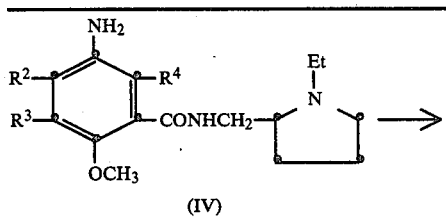

(IV)

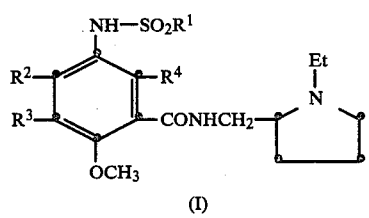

(I)

| Ex. No. | IV | | | I | m.p. (°C.) |
|---|---|---|---|---|---|
| | R² | R³ | R⁴ | R¹ | |
| 6 | F | H | H | Me | 128.5-130 |
| 7 | Cl | H | H | Et | 138-139 |
| 8 | Cl | H | H | Pr | 131-132 |
| 9 | Da | H | H | Me | 119-120.5 |
| 10 | H | H | H | Et | 156-157 |
| 11 | H | H | H | Da | 141-142 |
| 12 | H | H | H | Bu | 130-131.5* |
| 13 | H | Met | H | Me | 119-120 |
| 14 | Met | H | H | Me | 152-154 |
| 15 | Me | H | H | Et | 140-141 |
| 16 | Me | H | H | Me | 131-132 |
| 17 | Et | H | H | Me | 135-136 |
| 18 | H | Me | H | Et | 117-118 |
| 19 | Et | H | H | Et | 82-83.5 |
| 20 | H | Me | H | Me | 111.5-112.5 |
| 21 | Me | H | H | Da | 129-129.5 |
| 22 | Cl | H | H | Me | 146-146.5 |
| 23 | H | H | Cl | Me | 97-97.5 |

Note:
The abbreviations each have the following significance: Et (ethyl), Da (dimethylamino), Bu (butyl), Me (methyl), Met (methoxy), F (fluorine), H (hydrogen), Cl (chlorine)
*Hydrochloride of this product shows a melting point of 202 to 203° C. (decomp.)

EXAMPLE 24

To a solution of N-(1-cyclohexyl-3-pyrrolidinyl)-2-methoxy-5-aminobenzamide (1.0 g) in dry pyridine (5 ml), methanesulfonyl chloride (308 mg) is added with ice cooling, and the reaction mixture is stirred at room temperature for 20 minutes. The reaction mixture is worked up as in Example 1 to give N-(1-cyclohexyl-3-pyrrolidinyl)-2-methoxy-5-methanesulfonamidobenzamide (731 mg) as crystals melting at 170° to 171.5° C.
Anal. Calcd. for $C_{19}H_{29}O_4N_3S$: C,57.70; H,7.39; N,10.62; S,8.11. Found: C,57.89; H,7.47; N,10.45; S,8.37.

EXAMPLE 25

(1) To a mixture of methyl 2-methoxy-5-aminobenzoate (300 mg), dry methylene chloride (6 ml), and triethylamine (368 mg), a solution of methanesulfonyl chloride (400 mg) in dry methylene chloride (1 ml) is added dropwise with ice cooling, and the resultant mixture is stirred at room temperature for 1 hour. The reaction mixture is made alkaline with aqueous sodium hydrogencarbonate and shaken with methylene chloride. The organic layer is washed with water, dried over sodium sulfate, and evaporated under reduced pressure to remove the methylene chloride. The residue is washed with ethyl acetate/isopropyl ether to give methyl 2-methoxy-5-N,N-bis(methanesulfonyl)aminobenzoate (520 mg), which is recrystallized to give crystals melting at 169° to 169.5° C.
Anal. Calcd. for $C_{11}H_{15}O_7NS_2$: C,39.16; H,4.48; N,4.15; S,19.01. Found: C,39.04; H,4.45; N,4.04; S,19.01.

(2) To a mixture of tetrahydrofuran (3 ml) and 10% aqueous sodium hydroxide (3 ml), above product (300 mg) is added, and the resultant mixture is stirred with heating at 50° C. for 1.25 hours. After evaporating the reaction mixture under reduced pressure to remove the solvent, the residue is acidified with 6 N hydrochloric acid, salted out with sodium chloride, and shaken with methylene chloride containing a small amount of methanol. The organic layer is washed with saturated brine, dried over sodium sulfate, and evaporated under reduced pressure to remove the solvent. The residue is washed with isopropyl ether to give 2-methoxy-5-methanesulfonamidobenzoic acid (175 mg) as crystals melting at 166° to 167.5° C.

(3) A mixture of above product (150 mg) and thionyl chloride (3 ml) is refluxed with heating for 30 minutes. After evaporating the reaction mixture under reduced pressure to remove the thionyl chloride, the residue is mixed with dry benzene and evaporated again under reduced pressure to remove the solvent. The residue is dissolved in dry methylene chloride (3 ml). To this solution, triethylamine (124 mg) and a solution of 1-ethyl-2-aminomethylpyrrolidine (90 mg) in dry methylene chloride (1 ml) is dropwise in that order added with ice cooling, and the resulting mixture is stirred at room temperature for 15 minutes. The reaction mixture is made alkaline with aqueous sodium hydrogencarbonate, salted out with sodium chloride, and shaken with methylene chloride. The organic layer is washed with saturated brine, dried over sodium sulfate, and evaporated under reduced pressure to remove the methylene chloride. The residue is chromatographed on a column of alumina, which is eluted with 1% methanol/methylene chloride-2% methanol/methylene chloride. After evaporating the eluate to remove the solvent, the residue is recrystallized from ethyl acetate/isopropyl ether to give N-(1-ethyl-2-pyrrolidinylmethyl)-2-methoxy-5-methanesulfonamidobenzamide (143 mg). The product is recrystallized from ethyl acetate/isopropyl ether to give crystals melting at 171° to 172° C.

EXAMPLE 26

(1) To a solution of methyl 2-methoxy-5-aminobenzoate (300 mg) and dry pyridine (3 ml), methanesulfonyl chloride (210 mg) is added dropwise with ice cooling and stirring, and the resultant mixture is stirred at room temperature for 1 hour. The reaction mixture is acidified with 6 N hydrochloric acid and shaken with methylene chloride. The organic layer is washed with water, dried over sodium sulfate, and evaporated under reduced pressure to remove the methylene chloride. The residue is chromatographed on a column of silica gel, which is eluted with methylene chloride-2% methanol/methylene chloride, and the eluate is evaporated to remove the solvent. The residue is recrystallized from ethyl acetate/isopropyl ether to give methyl 2-methoxy-5-methanesulfonamidobenzoate (381 mg) as colorless prisms melting at 84° to 86° C.
Anal. Calcd. for $C_{10}H_{13}O_5NS.1/10H_2O$: C,46.32; H,5.05; N,5.40; S,12.37. Found: C,45.77; H,5.14; N,5.30; S,12.32. (2) A solution of above product (330 mg), 1-ethyl-2-aminomethylpyrrolidine (245 mg) and n- propanol (7 ml) is refluxed for 23 hours with heating. After cooling, the reaction mixture is evaporated under reduced pressure to remove the n-propanol and the residue is dissolved in dilute hydrochloric acid. The acidic solution is shaken with methylene chloride to remove the unreacted ester. The hydrochloric acid layer is made alkaline with sodium hydrogencarbonate, salted out with sodium chloride, and shaken with methylene chloride. The organic layer is washed with saturated brine, dried over sodium sulfate, and evaporated under reduced pressure to remove the methylene chloride. The residue is chromatographed on a column of alumina, which is eluted with 2% methanol/methylene chloride. The eluate is evaporated to remove the solvent. The residue is recrystallized from ethyl acetate/isopropyl ether to give N-(1-ethyl-2-pyrrolidinylmethyl)-2-methoxy-5-methanesulfonamidobenzamide (143 mg) as colorless scales melting at 171° to 172° C.

EXAMPLE 27

Using N-(1-ethyl-2-pyrrolidinylmethyl)-2-methoxy-4-chloro-5-methanesulfonamidobenzamide and dimethyl sulfate, the reaction is effected as in Example 5, whereby N-(1-ethyl-2-pyrrolidinylmethyl)-2-methoxy-4-chloro-5-(N-methylmethanesulfonamido)benzamide is obtained as crystals melting at 140.5° to 142° C.

EXAMPLE 28

(1) To a mixture of N-(1-ethyl-2-pyrrolidinylmethyl)-2-methoxy-4-methyl-5-aminobenzamide (1.0 g), dry methylene chloride (20 ml), and triethylamine (693 mg) is added dropwise a mixture of t-butylaminosulfonyl chloride (707 mg) and methylene chloride (5 ml) with ice cooling and stirring. After stirring for 15 minutes, the reaction mixture is mixed with aqueous sodium hydrogencarbonate and shaken with methylene chloride. The organic layer is washed with water, dried over sodium sulfate, and evaporated to remove the solvent. The residue is chromatographed on a column of alumina and eluted with 0-2% methanol/methylene chloride. The eluate is recrystallized from ethyl acetate/isopropyl ether to give N-(1-ethyl-2-pyrrolidinylmethyl)-2-methoxy-4-methyl-5-t-butylaminosulfonamidobenzamide (1.0 g) as crystals melting at 167° to 168° C.

Anal. Calcd. for $C_{20}H_{34}O_4N_4S$: C, 56.31; H, 8.03; N, 13.13; S, 7.52. Found: C, 56.23; H, 8.11; N, 12.84; S, 7.70.

(2) Above product (700 mg) is mixed with trifluoroacetic acid (7 ml), stirred at room temperature for 3 hours, and evaporated to remove the trifluoroacetic acid. The residue is mixed with aqueous ammonia, salted out with saturated brine, and shaken with chloroform. The organic layer is washed with saturated brine, dried over sodium sulfate, and recrystallized from ethyl acetate/ether to give N-(1-ethyl-2-pyrrolidinylmethyl)-2-methoxy-4-methyl-5-aminosulfonamidobenzamide (408 mg) as crystals melting at 140° to 141° C.

Anal. Calcd. for $C_{16}H_{20}O_4N_4S$: C, 51.87; H, 7.07; N, 15.12; S, 8.65. Found: C, 51.87; H, 7.07; N, 14.81; S, 8.63.

EXAMPLES 29–32

Using the following starting materials (I'), the reactions are effected as in Example 28, whereby the corresponding products (I) and (I$^b$) are obtained.

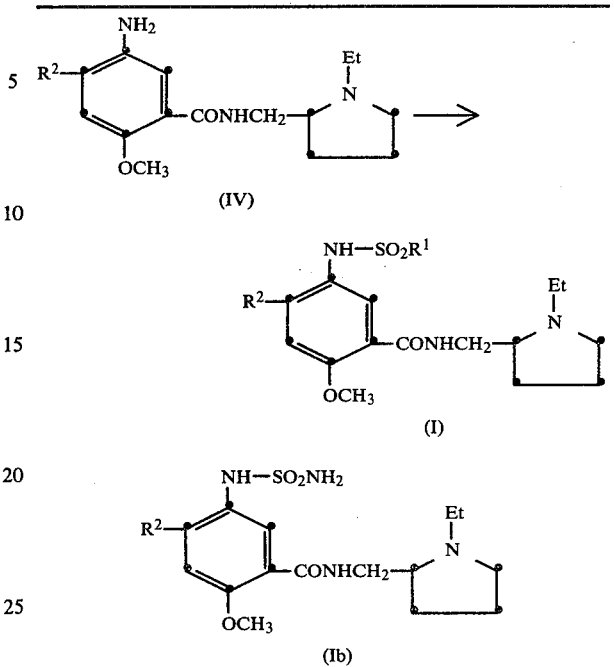

| EX. No. | IV R$^2$ | I R$^1$ | m.p. (°C.) | Ib m.p. (°C.) |
|---|---|---|---|---|
| 29 | Cl | NH(t-Bu) | 141–142 | 158–159 |
| 30 | Cl | piperidino | 139–141 | — |
| 31 | Me | NH—Me | 157–158 | — |
| 32 | H | NH(t-Bu) | — | 140–141 |

Note:
The abbreviation has the following significance: t (tertiary)

EXAMPLE 33

(1) A mixture of 2-methoxy-4-methyl-5-methanesulfonamidobenzoic acid (20 g) and thionyl chloride (20 ml) is refluxed for 2.5 hours, and the reaction mixture is evaporated under reduced pressure to remove the thionyl chloride. The residue is mixed with dry benzene (10 ml) and triethylamine (1.5 g), then a mixture of tetrahydrofurfurylamine (870 mg) and dry benzene (2 ml) is added with ice cooling and stirring, and the resultant mixture is stirred at room temperature for 15 minutes. The reaction mixture is made alkaline with sodium hydrogencarbonate and shaken with methylene chloride. The organic layer is washed with water, dried over sodium sulfate, and evaporated to remove the methylene chloride. The residue is washed with ethyl acetate/isopropyl ether to give N-tetrahydrofurfuryl-2-methoxy-4-methyl-5-methanesulfonamidobenzamide (2.21 g) as crystals melting at 207° to 208.5° C.

(2) A mixture of above product (1.5 g), thionyl chloride (9 ml), and chloroform (30 ml) is refluxed for 4 hours. The reaction mixture is poured into icy water and shaken with methylene chloride, and the organic layer is washed with aqueous sodium hydrogencarbonate and water in that order and dried over sodium sulfate and evaporated. The residue is dissolved in methylene chloride and chromatographed on a column of silica gel, which is eluted with 1% methanol/methylene chloride. After removing the solvent from the eluate, the residue is washed with ethyl acetate/ether to give N-(2,5-dichloropentyl)-2-methoxy-4-methyl-5- methanesulfonamidobenzamide (1.30 g) as crystals melting at 132° to 132.5° C.

(3) A solution of above product (100 mg) and 70% aqueous ethylamine is warmed at 60° C. for 2.5 hours. The reaction mixture is cooled with ice, mixed with aqueous sodium hydrogencarbonate, salted out with sodium chloride, and shaken with methylene chloride. The organic layer is washed with saturated brine, dried over sodium sulfate, and evaporated to remove the solvent. The residue is chromatographed on a column of alumina and eluted with 1% methanol/methylene chloride. After evaporating the eluate to remove the solvent, the residue is washed with ethyl acetate/isopropyl ether to give N-(1-ethyl-2-pyrrolidinylmethyl)-2-methoxy-4-methyl-5-methanesulfonamidobenzamide (42 mg) as crystals melting at 131.5° to 133° C.

EXAMPLE 34

(1) Using 2-methoxy-4-chloro-5-nitrobenzoic acid, the reaction is effected as in Example 33 (1), whereby N-tetrahydrofurfuryl-2-methoxy-4-chloro-5-nitrobenzamide (3.85 g) is obtained as crystals melting at 164° to 165° C.

A solution of above product (3.65 g), conc. hydrochloric acid (36.5 ml), water (18 ml), tetrahydrofuran (36.5 ml), and tin chips (4.13 g) is heated at 50° C. for 2 hours. The reaction mixture is evaporated to remove the solvent. The residue is mixed with icy water, made strongly alkaline with sodium hydroxide, and shaken with methylene chloride. The organic layer is filtered to remove the insoluble part, washed with water, dried over sodium sulfate, evaporated to remove the solvent, and recrystallized from ethyl acetate/ether to give N-tetrahydrofurfuryl-2-methoxy-4-chloro-5-aminobenzamide as crystals melting at 109° to 110° C.

Above product (3.6 g) is dissolved in methylene chloride (36 ml) and triethylamine (2.85 g), then mixed with methanesulfonyl chloride (3.08 g) and methylene chloride (7.2 ml) with ice cooling and the resultant mixture is heated around the boiling point of the solvent for 30 minutes with stirring. The reaction mixture is shaken with aqueous sodium hydrogencarbonate. The methylene chloride layer is washed with water, dried over sodium sulfate, and evaporated to remove the solvent. The residue is mixed with 10% aqueous sodium hydroxide (61 ml) and tetrahydrofuran (10 ml) and stirred at 50° C. for 1.25 hour. The resultant mixture is acidified with conc. hydrochloric acid, shaken with methylene chloride, washed with water, dried over sodium sulfate, and evaporated to remove the solvent. The residue is washed with ethyl acetate/ether and recrystallized from methylene chloride/ethyl acetate to give N-tetrahydrofurfuryl-2-methoxy-4-chloro-5-methanesulfonamidobenzamide (2.82 g) as crystals melting at 159° to 160° C.

(2) Using the above product, the reaction is effected as in Example 33 (2), whereby N-(2,5-dichloropentyl)-2-methoxy-4-chloro-5-sulfonamidobenzamide is obtained as crystals melting at 105° to 106.5° C.

(3) Using above product (1.3 g) and 70% aqueous ethylamine (26 ml), the reaction is effected as in Example 33 (3), whereby N-(1-ethyl-2-pyrrolidinylmethyl)-2-methoxy-4-chloro-5-methanesulfonamidobenzamide (452 mg) is obtained as crystals melting at 126° to 127.5° C.

EXAMPLE 35

(1) To a solution of 2-methoxy-4-methyl-5-nitrobenzoyl chloride (7.0 g), methylene chloride (35 ml) and triethylamine (7.68 g) is added a mixture of tetrahydrofurfurylamine (4.33 g) and dry benzene (11 ml) with ice cooling and stirring. The resultant mixture is allowed to stand at room temperature for 20 minutes, mixed with water and shaken with methylene chloride. The organic layer is dried over sodium sulfate and evaporated to remove the solvent. The residue is washed with ethyl acetate/isopropyl ether and recrystallized from methylene chloride/ethyl acetate to give N-tetrahydrofurfuryl-2-methoxy-4-methyl-5-nitrobenzamide (7.1 g) as crystals melting at 178° to 179.5° C.

Above product (8.1 g) is reduced in a conventional manner using platinum oxide (810 mg) and methanol (162 ml) to give N-tetrahydrofurfuryl-2-methoxy-4-methyl-5-aminobenzamide (7.81 g) as an oil.

A mixture of above product (500 mg), dimethylsulfamoyl chloride (543 mg), triethylamine (382 mg), and dry benzene (10 ml) is refluxed for 18 hours. The reaction mixture is evaporated to remove the solvent, made alkaline with 10% aqueous sodium hydroxide, and shaken with ether. The alkaline solution is acidified with 6 N hydrochloric acid and shaken with methylene chloride. The organic layer is dried over sodium sulfate and evaporated to remove the solvent to give a gelatinous product, which is chromatographed on a column of silica gel and eluted with 2% methanol/methylene chloride. The eluate is evaporated to remove the solvent, and the residue is washed with ethyl acetate/isopropyl ether to give N-tetrahydrofurfuryl-2-methoxy-4-methyl-5-dimethylaminosulfonamidobenzamide (315 mg) as crystals melting at 130° to 131° C.

(2) Using above product (700 mg), thionyl chloride (4.2 ml), and chloroform (14 ml), the reaction is effected as in Example 33 (2), whereby N-(2,5-dichloropentyl)-2-methoxy-4-methyl-5-dimethylaminosulfonamidobenzamide (618 mg) is obtained as an oil.

(3) Using above product and 70% aqueous ethylamine (3.1 ml), the reaction is effected as in Example 33 (3), whereby N-(1-ethyl-2-pyrrolidinylmethyl)-2-methoxy-4-methyl-5-dimethylaminosulfonamidobenzamide (305 mg) is obtained as crystals melting at 126° to 128° C.

EXAMPLES 36–39

Using the following starting materials (II) and the amine (III) the reactions are effected as in Example 33 (3), whereby the corresponding products (I) are obtained.

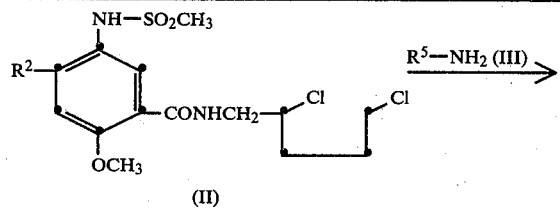

(II)

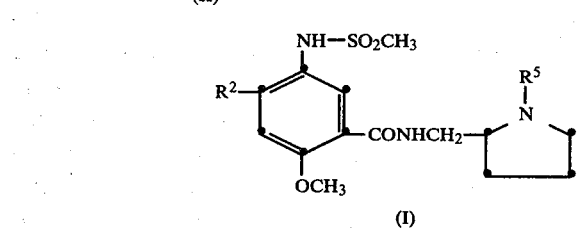

(I)

| Ex. No. | R² | R⁵ | m.p. (°C.) |
|---|---|---|---|
| 36 | Me | allyl | 141.5–143 |
| 37 | Me | benzyl | 125–129 |
| 38 | Cl | allyl | 118–118.5 |
| 39 | Cl | p-fluorobenzyl | 138–142 |

EXAMPLE 40

A mixture of N-(1-ethyl-2-pyrrolidinylmethyl)-2-methoxy-4-methyl-5-methanesulfonamidobenzamide (500 mg), triethylamine (823 mg), dimethylaminosulfonyl chloride (1.17 g), and methylene chloride (20 ml) is refluxed for 39 hours. The reaction mixture is washed with aqueous sodium hydrogencarbonate. The organic layer is washed with water, dried over sodium sulfate, and evaporated to remove the solvent. The residue is chromatographed on a column of alumina and eluted with 0.5–1% methanol/methylene chloride. The eluate is evaporated to give N-(1-ethyl-2-pyrrolidinylmethyl)-2-methoxy-4-methyl-5-[N-(dimethylaminosulfonyl)methanesulfonamido]benzamide (351 mg) as an oil. This product is mixed with tetrahydrofuran (3 ml) and 10% sodium hydroxide (3 ml) and warmed at 80° C. for 1 hour. The reaction mixture is evaporated to remove the tetrahydrofuran, acidified with hydrochloric acid, made alkaline with sodium hydrogencarbonate, salted out with sodium chloride, and shaken with methylene chloride. The organic layer is washed with saturated brine, dried over sodium sulfate, and evaporated to remove the solvent. The residue is chromatographed on a column of alumina and eluted with 3% methanol/methylene chloride. The eluate is evaporated to remove the solvent. The residue is washed with ether/isopropyl ether and filtered to give N-(1-ethyl-2-pyrrolidinylmethyl)-2-methoxy-4-methyl-5-dimethylaminosulfonamidobenzamide (211 mg). The product is recrystallized from acetonitrile/isopropyl ether to give crystals melting at 129° to 129.5° C.

EXAMPLE 41

| | |
|---|---|
| N-(1-Ethyl-2-pyrrolidinylmethyl)-2-methoxy-4-methyl-5-dimethylaminosulfonamidobenzamide | 100 g |
| Lactose | 192 g |
| Wheat starch | 96 g |
| Carboxymethyl cellulose sodium | 10 g |
| Magnesium stearate | 2 g |

These ingredients are admixed, kneaded with water, and granulated with a granulator in a conventional manner. The resulting granules are sieved through a 20 mesh sieve and made into 2000 tablets each containing 50 mg of the effective ingredient and weighing 200 mg. The tablets are coated with syrup to give sugar coated tablets.

What we claim is:

1. A process for preparing a compound of the formula:

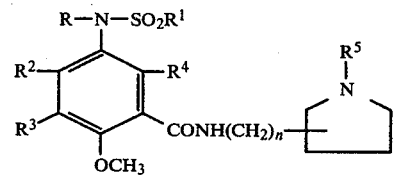

wherein
R is hydrogen, C₁–C₆ alkyl, cyano or C₁–C₆ alkanesulfonyl,
R¹ is C₁–C₆ alkyl, phenyl, amino, C₁–C₆ alkylamino, C₂–C₁₂ dialkylamino or C₄–C₅ alkyleneamino,
R² is hydrogen, halogen, C₁–C₆ alkyl, C₂–C₁₂ dialkylamino or C₁–C₆ alkoxy,
R³ is hydrogen, methyl or methoxy,
R⁴ is hydrogen or halogen,
R⁵ is C₁–C₆ alkyl, C₂–C₆ alkenyl, C₃–C₆ cycloalkyl, benzyl or halobenzyl, and
n is zero or 1, or a pharmaceutically acceptable acid addition salt of said compound, which comprises the steps of reacting a tetrahydrofuryl compound of the formula:

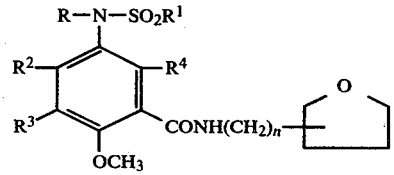

wherein R, R¹, R², R³, R⁴ and n are each as defined above, with thionyl chloride in an inert solvent at a temperature above room temperature, and isolating and reacting the resultant dichloro compound of the formula:

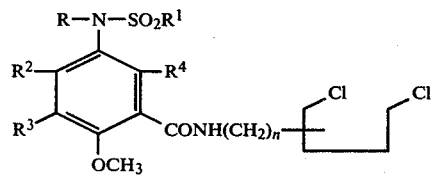

wherein R, R¹, R², R³, R⁴ and n are each as defined above, with an amino compound of the formula:

R⁵—NH₂ wherein R⁵ is as defined above, in the presence or absence of a suitable solvent at a temperature above room temperature.

2. A process as claimed in claim 1, wherein R in the resulting product is hydrogen, and said product is subjected to C₁–C₆ alkylation in the presence of an inorganic base in an inert solvent at a temperature of from above room temperature to the boiling point of the solvent, to convert R to a C₁–C₆ alkyl group.

* * * * *